(12) United States Patent
Li et al.

(10) Patent No.: US 11,357,728 B2
(45) Date of Patent: Jun. 14, 2022

(54) LIPOSOME HAVING INNER WATER PHASE CONTAINING SULFOBUTYL ETHER CYCLODEXTRIN SALT

(71) Applicant: CSPC ZHONGQI PHARMACEUTICAL TECHNOLOGY (SHIJIAZHUANG) CO., LTD., Hebei (CN)

(72) Inventors: Chunlei Li, Hebei (CN); Lan Zhang, Hebei (CN); Caixia Wang, Hebei (CN); Li Zhang, Hebei (CN); Dongmin Shen, Hebei (CN); Yanhui Li, Hebei (CN); Xian Xiu, Hebei (CN); Min Liang, Hebei (CN); Yongfeng Li, Hebei (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 0 days.

(21) Appl. No.: 14/496,215

(22) Filed: Sep. 25, 2014

(65) Prior Publication Data
US 2015/0030672 A1 Jan. 29, 2015

Related U.S. Application Data

(63) Continuation-in-part of application No. 13/502,776, filed as application No. PCT/CN2010/078115 on Oct. 26, 2010, now Pat. No. 8,871,253.

(30) Foreign Application Priority Data

Oct. 26, 2009 (CN) .......................... 200910075783.9

(51) Int. Cl.
| A61K 9/127 | (2006.01) |
| A61K 31/136 | (2006.01) |
| A61K 31/4745 | (2006.01) |
| A61K 31/704 | (2006.01) |
| A61K 31/475 | (2006.01) |

(52) U.S. Cl.
CPC .......... *A61K 9/1278* (2013.01); *A61K 9/1271* (2013.01); *A61K 31/136* (2013.01); *A61K 31/475* (2013.01); *A61K 31/4745* (2013.01); *A61K 31/704* (2013.01)

(58) Field of Classification Search
None
See application file for complete search history.

(56) References Cited

U.S. PATENT DOCUMENTS

| 5,837,282 A * | 11/1998 | Fenske ................. A61K 9/1278 264/4.1 |
| 5,858,397 A * | 1/1999 | Lim et al. ..................... 424/450 |
| 6,465,008 B1 | 10/2002 | Slater et al. |
| 2002/0146450 A1 | 10/2002 | Slater et al. |
| 2005/0164986 A1 | 7/2005 | Mosher et al. |
| 2006/0258537 A1 | 11/2006 | Stella et al. |
| 2007/0014845 A1 | 1/2007 | Zhang et al. |
| 2009/0081121 A1* | 3/2009 | Ting et al. .................. 424/1.21 |
| 2009/0196918 A1 | 8/2009 | Joguparthi et al. |
| 2012/0128757 A1* | 5/2012 | Kikuchi et al. ............... 424/450 |

FOREIGN PATENT DOCUMENTS

| CN | 102038640 A | 5/2011 |
| CN | 102038641 A | 5/2011 |
| WO | WO-2010-113983 | * 10/2010 |

OTHER PUBLICATIONS

Lockwood S, Improved Aqueous Solubility of Crystalline Astaxanthin by Captisol, J Pharma Sci, 92, 4, 2003, 922.*
Abmole, 2010 (http://www.abmole.com/products/captisol.html).*
Budau et al (Journal of the Chilean Chemical Society, 62(3) 2017).*
Abraham, Sheela A. "An evaluation of transmembrane ion gradient-mediatedencapsulation of topotecan within liposomes", Journal of Controlled Release 96, 2004, pp. 449-461.
Beta-cyclodextrin sulfobutyl ether sodium salt, Captisol (Cydex), 2006, The Merck Index.
Drummond, Daryl C., et al. "Improved Pharmacokinetics and Efficacy of a HighlyStable Nanoliposomal Vinorelbine", The Journal of Pharmacology and Experimental Therapeutics, 2009, vol. 238, No. 1, pp. 321-330.
International Search Report for International Application No. PCT/CN2010/078115, dated Feb. 10, 2012, with English translation.
Lockwood, Samuel F., et al. "Improved aqueous solubility of crystalline astaxanthin (3,3—dihydroxy-beta-beta-carotene-4, 4-dione) by Captisol (Sulfobutyl ether beta-cyclodextrin)", JPharmSci, 2003, 92(4), 922-926.
Semple, Sean C. et al. "Optimization and Characterization of a Sphingomyelin/Cholesterol Liposome Formulation of Vinorelbine with Promising Antitumor Activity", Journal of Pharmaceutical Sciences, vol. 94, No. 5, May 2005, p. 1024-1038.
Taggar, Amandeep S. "Copper-topotecan complexation mediates drug accumulation into liposomes", Journal of Controlled Release 114 (2006), pp. 78-88.
Yeh, Brian K. et al. "Structural Basis for Activation of Fibroblast Growth Factor Signalingby Sucrose Octasulfate", Molecular and Cellular Biology, Oct. 2002, p. 7184-7192.
Russian Office Action corresponding to Application No. 2012119799/15(029780); dated Oct. 26, 2010, with English translation.
Russian Second Office Action corresponding to Application No. 2012119799/15(029780); dated Feb. 5, 2015, with English translation.
Y.L. Knunianz, Chemical encyclopedia, vol. 1, Scientific publishing house "Great Russian encyclopedia", Moscow, 1998, p. 147, with English translation of relevant portion.

* cited by examiner

*Primary Examiner* — Celeste A Roney
(74) *Attorney, Agent, or Firm* — Seed IP Law Group LLP

(57) ABSTRACT

A liposome comprising bilayer and inner water phase is disclosed. Said inner water phase may contain sulfobutyl ether cyclodextrin and an active compound.

13 Claims, 2 Drawing Sheets

LIPOSOME HAVING INNER WATER PHASE CONTAINING SULFOBUTYL ETHER CYCLODEXTRIN SALT

CROSS REFERENCE TO RELATED APPLICATIONS

The present application is a continuation-in-part application of U.S. patent application Ser. No. 13/502,776, filed on Apr. 19, 2012, the entire contents of which are incorporated herein by reference and priority to which is hereby claimed. Application Ser. No. 13/502,776 is the U.S. National stage of application No. PCT/CN2010/078115, filed Oct. 26, 2010. Priority under 35 U.S.C. § 119(a) and 35 U.S.C. § 365(b) is hereby claimed from Chinese Application No. 200910075783.9, filed Oct. 26, 2009, the disclosure of which is also incorporated herein by reference.

FIELD OF THE INVENTION

The present invention relates to a liposome having inner water phase containing sulfobutyl ether cyclodextrin salt, to methods for manufacturing the liposome and to the use thereof in preparing a medicament for the treatment of tumor diseases.

BACKGROUND OF THE INVENTION

As a carrier of drugs, a liposome has the characteristics such as enhancing therapeutic efficacy, reducing adverse effects, target delivering, and delayed release. Especially where a liposome is used as the carrier of anti-tumor drug, the drug can be targetedly delivered to tumor area and thus has reduced toxicity and enhanced efficacy.

There are many anti-tumor drugs in clinical application which can be categorized into 5 groups: cytotoxic agents, hormones, biological response modifier, monoclonal antibodies and other anti-tumor drugs. Among them, cytotoxic agents capture the biggest market share, and they can be categorized into 5 groups according to mechanism of action: (1) drugs acting on DNA chemical structure, such as alkylating agents and platinum compounds; (2) drugs modifying nucleic acid synthesis, such as methotrexate and fluorouracil; (3) drugs acting on nucleic acid transcription, such as doxorubicin and epidoxorubicin; (4) drugs acting on tubulin synthesis, such as taxanes and vinca alkaloids; drugs acting on topoisomerase, such as camptothecin; (5) other cytotoxic drugs. Among them, the drugs of groups (2) and (4) are of cell cycle-specific character, can only kill cells in specific period of malignant tumor cell proliferation cycle. Vinorelbine and topotecan are of the groups and are intensively investigated in the present invention.

It is necessary to control the drug release from liposome with the aim of reducing toxicity and enhancing efficacy, where anti-tumor drug with cell cycle-specific character is prepared into liposome. In case of too fast drug releases from liposome, the following results will be incurred: (1) part of drug is released from liposome before reaching tumor area and is cleared from blood too quickly to reach tumor area; (2) in view that tumor cells are in different growth periods at the same time, the drug reaching tumor area can not kill cells out of specific periods, which induces greatly reduced exposure of the drug to tumor cells and has a poor therapeutic efficacy but induces toxic response of normal tissues. So it is important to control the drug release from liposome especially for the drugs with cell cycle-specific character.

The release of liposomal drug is influenced by diversified factors including particle size, lipid membrane composition, inner water phase and methods of drug loading, inter alia. Methods of drug loading include active drug loading and passive drug loading. Passive drug loading is generally suitable for lipid-soluble drugs, while active drug loading is generally suitable for water-soluble drugs. Since vinorelbine and topotecan are both water-soluble weak alkalescent drugs, active drug loading is chosen to prepare their liposomes. Three methods of active drug loading are commonly used in the art: pH gradient method, ammonium sulfate gradient method and complexation gradient method.

(1) pH Gradient Method:

This method is invented by Canadian investigators in the 1980's. They discovered that pharmaceutical alkaloids such as doxorubicin could be actively transported and specifically aggregated into liposomes in the presence of pH gradient. The first thing in the process of preparation is to choose inner water phase buffer and outer phase buffer, which is critical since the buffers directly determines the stability of drug in storage and the release of drug in vivo. A blank liposome is formed by hydration with inner water phase buffer. The thus-obtained blank liposome is further processed to reduce the particle size within a desired range. Next, outer phase of the liposome may be replaced by using the technical means such as cross flow dialysis, column chromatography and pH modulation, so as to form pH gradient between outer and inner transmembrane phases. The drug loading may be accomplished at an appropriate temperature after the transmembrane gradient is formed.

Also the transmembrane pH gradient can be formed using an ionophore. During the preparation of the blank liposome, divalent ion salt, such as manganese sulfate, is encapsulated into the liposome, and then the outer phase of liposome is replaced by a buffer containing an ionophore, such as A23187 and EDTA. The ionophore can specifically transport divalent ion to outside of membrane and transport $H^+$ to inside of liposome. Use of the above method can also form pH gradient between inside and outside of the membrane.

The mechanism of drug loading by pH gradient has been intensively investigated. Among 3 anthracycline liposome preparations available in the market, 2 preparations are prepared by active drug loading using pH gradient.

(2) Ammonium Sulfate Gradient Method

Ammonium sulfate gradient method is invented by Israeli investigators in early 1990's. The preparation process in this method is similar to that in traditional pH gradient method. First, blank liposome is prepared by using ammonium sulfate buffer. Then, ammonium sulfate in outer phase of the liposome is removed by cross flow dialysis inter alia to form ammonium sulfate gradient between the inside and the outside of lipid membrane. Then drug loading is accomplished under the condition of heating. It is confirmed in initial research that the drug loading by ammonium sulfate gradient may be related to pH difference between the inside and the outside of the phospholipid membrane caused by transmembrane diffusion of free ammonia. However, it is shown by strict theoretical deduction that the drug loading using ammonium sulfate gradient method may be a complicated process of double-directional diffusion, and the formation of pH gradient may be merely one of the factors.

The advantage of ammonium sulfate gradient method lies in that approximately neutral pH of the ammonium sulfate aqueous solution could not induce hydrolyzation of excess phospholipid molecules, because a relatively high temperature is required if saturated phospholipid is used to prepare the liposome. The lipid is apt to hydrolyze when traditional pH gradient method is used. Moreover, the in vivo drug release of the liposome prepared using ammonium gradient method may be different.

(3) Complexation Gradient Method

In this method, transition metal ion salt, such as copper sulfate or nickel sulfate is used in inner water phase buffer to prepare blank liposome. Next, metal ion outside the liposome is removed by cross flow dialysis among others to form the metal ion gradient between the inside and the outside of lipid membrane. Then drug loading is accomplished under the condition of heating. The mechanism of drug loading is that the drug forms a stable complex with transition metal ion in the inner water phase of liposome and is thus restrained within liposome.

As the first-line drugs in anti-tumor therapy, liposomal preparations of vinorelbine and topotecan have been intensively investigated. Now the drug loading of liposomal vinorelbine and topotecan have been investigated by many research groups. However, some problems rise such as the following:

Inex company of Canada achieves the drug loading by using sphingomyelin and cholesterol at a molar ratio of 55:45 as lipid membrane, using a solution of magnesium sulfate (450 mM) as inner water phase to prepare blank liposome, then transporting magnesium ion out of the liposomal membrane via the ionophore A23187 (the amount of added ionophore is 1 µg/mg lipid), and transporting $H^+$ to inside of liposome, and thus generating pH gradient. The thus-obtained liposomal vinorelbine has an encapsulation rate of more than 90%, and is stable when stored at 2-8° C. for one year. Because the ionophore can be toxic to cells and animals, it is necessary to strictly control the residue of ionophore in the formulation. The researchers need to perform a further dialysis on the liquid after the drug loading is completed, so that the final residue of ionophore in the final liquid is less than the usually accepted safety standard, 50 ng/mg phospholipid. (Optimization and characterization of a sphingomyelin/cholesterol liposome formulation of vinorelbine with promising antitumor activity. Journal of Pharmaceutical Sciences, 2005 Vol. 94 No. 5.)

A Canadian research group leaded by Bally used two methods and obtained topotecan liposomes having high encapsulation rate. In the first method, DSPC and cholesterol are used as lipid membrane, a 300 mM solution of manganese sulfate or manganese chloride as inner water phase to prepare a blank liposome. Then pH gradient is formed using the ionophore A23187 and the drug loading is achieved.

The amount of added ionophores was 250 ng/mg lipid. The mechanism of this method is similar to that used by Inex company. But this method did not perform the step of removing ionophores after drug was loaded, so the residual metal ions in the preparation may produce toxicity in the blood. The second method uses DSPC and cholesterol as lipid membrane, copper sulfate solution as inner water phase to prepare blank liposome. However, the loading of topotecan is accomplished without adding A23187, because a stable complex is formed between copper ion and topotecan. The principle used herein is just the complexation gradient method as described above. (An evaluation of transmembrane ion gradient-mediated encapsulation of topotecan within liposomes. Journal of Controlled Release. 96 (2004); Copper-topotecan complexation mediates drug accumulation into liposomes. Journal of Controlled Release. 114 (2006)).

US investigators use distearoyl phosphatidyl choline (DSPC), cholesterol and distearoyl phosphatidyl ethanolamine-methoxyl-polyethylene glycol conjugate (DSPE-mPEG) as lipid membrane, use triethylamine (TA) salt of sucrose octasulfate as inner water phase to prepare blank liposome. Then TA sucrose octasulfate is removed using cross flow dialysis inter alia to form TA sucrose octasulfate gradient, and the loading of drug is accomplished. The principle is substantively identical to that used in ammonium sulfate gradient method. However, each sucrose octasulfate molecular has 8 acid groups and can form a tight complex with vinorelbine, and thus vinorelbine is well restrained. The plasma half-life of the thus-obtained vinorelbine liposome is up to 9.2 hours (Improved pharmacokinetics and efficacy of a highly stable nanoliposomal vinorelbine. The journal of Pharmacology and Experimental Therapeutics. 2009 Vol. 328 No. 1.). The serious concern in this method is that sucrose octasulfate is physiologically active and activates fibroblast growth factor in vivo (Structural basis for activation of fibroblast growth factor signaling by sucrose octasulfate. MOLECULAR AND CELLULAR BIOLOGY, Oct. 2002, Vol. 22, No. 20), and induce a series of physiological effects. Therefore, the use of sucrose octasulfate as an excipient for injection may have a great risk.

Alza company of US uses hydrogenated soybean phosphatidyl choline (HSPC), cholesterol and DSPE-mPEG as lipid membrane, uses polyanion polymer, such as dextran sulphate, proteoglycan sulphate and cellulose sulphate, in inner water phase. Then cross flow dialysis is used to replace outer phase and form a polymer gradient, and the drug loading is accomplished. The principle is similar to that used in ammonium sulfate gradient method. This method has the aim of forming a tight complex of polyanion polymer with topotecan, and thus the drug is well restrained. The disadvantage of this method is also that the polyanion polymers are physiologically active and difficult to be metabolized in vivo, so the safety thereof shall be further investigated (Liposome-entrapped topoisomerase inhibitors. US6465008B1).

It is known from the above that the investigations of liposomes of weak alkalescent drugs, such as vinorelbine and topotecan focus on pH gradient method, general ammonium sulfate gradient method and complexation gradient method. However, they are only tested in laboratory and the materials used have safety risk: (1) the polyanionic salt, such as triethylamine salt of sucrose octasulfate and sulfate polymer, used in the above investigations are all physiologically active, and do not meet the requirement that an excipient should be inactive of physiology and of pharmacology; (2) copper ion, nickel ion, manganese ion used in the above complexation gradient method are all heavy metal ion, and their remainder in the formulation are harmful to human. Moreover, because tumor is difficult to be cured and medication is generally a long time, the in vivo accumulation of heavy metal ion will go beyond the patient tolerance.

So it is still required to develop a novel liposome and corresponding method of drug loading.

SUMMARY OF THE INVENTION

The inventors have surprisingly found in the study that liposomes can be prepared by SBE-β3-CD, in order to achieve the effective seal and loading of active ingredient. In the invention, the SBE-β3-CD functions completely different from the cyclodextrin in the liposome inclusion in the prior art. In the present invention, the inventors break through the traditional thinking way, and use the polyanionic property of SBE-β3-CD, instead of using its cage-shape characteristic and forming an inclusion and then passive loading of drug. Specifically, a blank liposome comprising sulfobutyl ether cyclodextrin ammonium salt or metal salts thereof in the inner phase is firstly prepared, then the salt of sulfobutyl ether cyclodextrin in the outer phase of the blank liposome is removed, to form an anion gradient, and a metal cation ionophore is added to the outer phase of the blank liposome, to form a pH gradient, so as to load active ingredient actively. The present invention is particularly suitable for water soluble drugs, such as doxorubicin hydrochloride, topotecan hydrochloride, vincristine sulfate and the like, since they can enter into the inner water phase of the liposome without need to be prepared into a cyclodextrin inclusion, thus a good encapsulation can be achieved. If the water soluble drugs if only rely on the inclusion effect of the SBE-β3-CD, the liposome entrapment efficiency will be very low, which has been demonstrated in the working examples of the present invention. In fact, the purpose of the invention is not to solve the problem of entrapment of insoluble drugs, but to extend the residence time of water soluble alkalescence drugs in a liposome, so as to meet the clinical requirements.

The use of sulfobutyl ether cyclodextrin salt as inner water phase to load drug has a similar principle as that in the use of ammonium sulfate as inner water phase, by which the anion in inner water phase forms precipitate with the drug molecule and thus extend drug release. However, each sulfobutyl ether molecule has 6.5 $SO_3^{2-}$ at average, and can bind to multiple drug molecules simultaneously and form more complex precipitate structure. So high encapsulation rate is achieved, and the drug retention time is significantly extended in comparison to the liposome with ammonium sulfate as inner water phase.

On the other hand, compared with the pH value gradient method and the complex gradient method used in the prior art, the method of the present invention adopts the combination of the salt of SBE-CD and metal cation ionophores, allowing a lower addition amount (as low as 20 ng/mg lipid) of the ionophores, while achieving the same or better encapsulation effect, which is of great significance for the safety application especially for long-term application of a drug. Furthermore, the method of the present invention can save the further dialysis step, thus save the production time and cost, but also reduce the risk of penetration of drug during the dialysis process.

Specifically, in the present invention, a metal ion salt of SBE-CD, such as a sodium salt, a calcium salt, a magnesium salt, is used as inner aqueous phase of the liposome, and then ionophores that can transfer the corresponding ions are added to form a pH gradient, thus drug loading is achieved. The concentration of liposome inner aqueous phase SBE-CD in the present invention is comparable to that of sulfate and chloride of the prior art, but addition amount of metal cation ionophore is only 20 ng/mg lipid, which is far less than the amount 250 ng/mg lipid or 1 ug/mg lipid in the background technology, however, it can achieve an entrapment rate greater than 90%, which shows that the present invention can achieve an unexpected effect by using SBE-CD, which causes a complexation of the drug much stronger than the sulfate and chloride. In the prior art, due to a relatively high amount of ionophores, it may be toxic to cells and animals. The initial addition amount of the metal cation ionophore in the present invention is far less than the critical value of 50 ng/mg phospholipid generally accepted, so the present invention can save the further dialysis step.

Without limited by the theory, the following contents will attempt to explore the mechanisms related to drug loading methods in the prior arts. Firstly, the ammonium sulfate gradient method is analyzed, which comprises the following process: driven by concentration and pH difference, high-concentration drug in outer phase of the liposome overcomes resistance of lipid membrane (phospholipid bilayer) and comes into the inner water phase of the liposome. The drug which comes into the inner water phase is protonated and precipitates with $SO_4^{2-}$, and is restrained stably in the liposome. It is needed to dissociate from the precipitate and diffuse out from the liposome for drug release. Therefore, the microscopic structure and solubility of the precipitate determine the release rate of drug from the liposome and further determine the safety and effectiveness of the formulation.

The microscopic structure and complexity of the precipitate formed by the drug and $SO_4^{2-}$ are related to the spatial structure and weak alkalescence of the drug. Some drug, such as doxorubicin hydrochloride, is apt to form precipitate with $SO_4^{2-}$ due to its strong alkalescence. Moreover, the drug molecules can pile up on each other due to quasi-planar structure of the molecule. and a compact elongated precipitate is formed within the liposome as microscopically shown. Therefore, doxorubicin hydrochloride can be well restrained in the liposome and the half-life $t_{1/2}$ of its liposomal formulation in KM mice is more than 15 hours. To the contrary, other drugs, such as vinorelbine and topotecan, are weak alkalescent and thus have a poor ability to precipitate with $SO_4^{2-}$, and the drug molecules can not pile up on each other due to non-planar structure of the molecule. Therefore, the $t_{1/2}$ in KM mice is less than 5 hours even if the liposome is prepared by using the same lipid composition and method as those of the above doxorubicin hydrochloride liposome. The half-life is so short that most of the drug leaked out from the liposome in blood circulation and can not reach tumor area. Even a small ratio of the liposomal drug which reached tumor area will be released out quickly. It is undesired for anti-tumor drug with cell cycle-specific character to exert its effect. It is concluded that one of the critical factors for drug release is the complexity of the precipitate formed between drug and anion.

The ammonium sulfate gradient method is relatively suitable for anthracycline anticancer drugs having a planar structure (such as doxorubicin (adriamycin), epirubicin, pirarubicin, idarubicin, mitoxantrone), because they can achieve the intermolecular piling, and then form a strip dense precipitation with the salt in the inner phase, which facilitates the drug entrapment and retention.

As for the weakly alkalescent drugs vinorelbine, topotecan etc, because of their inherent weak alkalinity, they are not suitable for the ammonium sulfate gradient method, so an anion that can combine with these drugs and form dense precipitation becomes the key to solve the problem, and the multi anionic compounds with complex structure may be used to produce more stable complex.

It is experimentally demonstrated that efficient encapsulation of weak alkalescent drug, such as vinorelbine or topotecan, can be achieved in the present invention. In vitro release test and pharmacokinetic test confirm that, in comparison to the conventional ammonium sulfate inner water phase formulation, the release rate of the liposomal drug of the present invention is markedly extended. The present invention is also suitable for other anti-tumor drugs, such as vincristine and irinotecan, with similar weak alkalescence of vinorelbine and topotecan.

Sulfobutyl ether-β-cyclodextrin (SBE-β-CD) is an ionized derivative of β-cyclodextrin (β-CD) developed by Cydex of US in 1990's, which is the product of substitution reaction of β-CD with 1,4-butane sultone. The substitution may occur at hydroxyl group of position 2, 3, 6 in glucose unit of SBE-β-CD. SBE-β-CD is an excellent pharmaceutical excipient having the advantages such as good water-solubility, low nephrotoxicity and low haemolysis, and is licensed by FDA as an excipient for injection.

SBE-β-CD has a spacial steric configuration of cyclic cage structure, with hydrophilic shell and hydrophoric inner room, and has been so far used for solubilization by inclusion of many insoluble drugs, thus achieve solubilization of insoluble drugs in hydrophilic solvents, and has been used widely in various dosage forms such as injection, oral formulation, topical formulation inter alia. Wang Zhixuan & Deng Yingjie, et al. (Advances in liposome entrapped drug cyclodextrin complex delivery systems, Journal of Shenyang Pharmaceutical University, 2006 Vol. 23) review world-wide researches of liposome entrapped drug cyclodextrin complex. Fat soluble or water insoluble drug can not enter the inner water phase of liposome, thus it is usually present in the lipid bilayer membrane. Such an existing way has the following shortcomings, first it will affect the stability of membrane structure, then it limits loading amount of drug. If the insoluble drug is first prepared into a cyclodextrin inclusion which is water-soluble, and then the inclusion is entrapped in the inner aqueous phase of liposomes, the above problem can be solved. The liposome of this structure is called as cyclodextrin inclusion liposome.

Chakraborty used SBE-β-CD to investigate liposomal preparation of amphotericin B, with the aim of using solubilization by inclusion of insoluble drug by SBE-β-CD, and obtained a amphotericin B liposome with high inclusion rate and high drug loading (Therapeutic and hemolytic evaluation of in-situ liposomal preparation containing amphotericin-B complexed with different chemically modified β-cyclodextrins. J Pharm Pharmaceut Sci. 2003 Vol. 6, No. 2).

US patent application 2007/0014845 recites a method for preparing liposome, comprising first preparing a cyclodextrin inclusion of a compound, and then loading the inclusion into liposomes, wherein the compound is a hydrophobic compound, including proteins, peptides, nucleic acids, diagnostic reagents, cardiovascular drugs, antibiotics, cytotoxic drugs and the like. It is indicated in paragraph 0005 that the concentration of cyclodextrin in the cyclodexrin inclusion liposome should be greater than 100 mg/ml, and most preferably 400 mg/ml. In the present invention, the concentration of SBE-β-CD in the inner phase of the sulfobutyl ether cyclodextrin prepared is 80-200 mg/ml, significantly less than the concentration used in the US patent application, but can get better encapsulation efficiency. The US application recites in the paragraph 0022-0023 of the description records that the cyclodextrin in the cyclodextrin inclusion liposome is selected from a variety of cyclodextrin derivatives, including the SBE-β-CD sodium salt; and the drug is entrapped in the aqueous phase after formation of a inclusion with cyclodextrin. In the method of the present invention, the liposomes comprising sulfobutyl ether cyclodextrin in the inner phase can also adopt the SBE-β-CD sodium salt as the inner aqueous phase, however, for the method of the present invention, after the formation of blank liposomes comprising SBE-β-CD sodium salt in the water phase, metal cation ionophores are added, and sodium ions in the lipid membrane are pumped out, and hydrogen ions outer of the lipid membrane are pumped in, thus forming transmembrane pH gradient, so as to achieve the drug loading. The US application explicitly teaches that suitable drugs are the fat soluble drugs, including topoisomerase I inhibitors, such as camptothecin, hydroxycamptothecin, sn38 etc. In addition, the US patent application method has a very high loss rate of drug, for example, as recited in example 2 thereof, in the preparation process of liposomes, the loss rate of drug is as high as 81.5%, the reason might be the following: the inner phase of the liposome obtained by hydration only accounts for a very small part of the total volume, due to the inclusion of the drug and cyclodextrin as phospholipid hydration solution, while most of the drug inclusion in the outer aqueous phase of the liposome are removed in the following dialysis steps, so this method of passive loading is difficult to achieve good encapsulation of hydrophobic drugs.

To obtain liposomal preparations with good properties, a salt of sulfobutyl ether cyclodextrin should be prepared first, and then the liposome should be prepared using a proper method. The method used in the present invention comprises:

(A) Preparation of salts of sulfobutyl ether cyclodextrin: preparing aqueous solution of sulfobutyl ether cyclodextrin, and salifying with triethylamine, triethanolamine, ammonia, sodium hydroxide, potassium hydroxide or calcium hydroxide.

(B) Preparation of liposomes: dissolving lipid excipients in an organic solvent, removing the organic solvent by lyophilization and then obtaining a loose lipid powder, hydrating the lipid phase powder with aqueous solution of sulfobutyl ether cyclodextrin salt to form a blank liposome. Then reducing the particle size of the blank liposome by a micro-jet apparatus or a high pressure extrusion apparatus, removing the salt of sulfobutyl ether cyclodextrin in outer phase of the liposome by dialysis or column chromatography inter alia to form an anion transmembrane gradient. If the salt of sulfobutyl ether cyclodextrin used is a metal ion salt, the addition of metal ionophore is required. The metal ionophore can be inserted into phospholipid membrane to exchange internal metal ion and external hydrogen ion, and thus a pH gradient is formed. Then the liposomal preparation is obtained by incubation the drug solution and the liposome suspension.

Sulfobutyl ether cyclodextrin used in the present invention shall be imported currently. However, it can be produced in bulk with good quality and meet the need of large scale production.

In summary, in the present invention, use of salts of sulfobutyl ether cyclodextrin as liposome inner water phase is completely feasible in consideration of drug encapsulation, retention effect and economic cost.

According to some embodiments of the liposome in the present invention, wherein the sulfobutyl ether cyclodextrin is sulfobutyl ether-α-cyclodextrin, sulfobutyl ether-β-cyclodextrin or sulfobutyl ether-γ-cyclodextrin.

According to some embodiments of the liposome in the present invention, wherein each sulfobutyl ether cyclodextrin molecule has about 6.5 sulfo groups at average.

According to some embodiments of the liposome in the present invention, wherein the salt of sulfobutyl ether cyclodextrin is formed by sulfobutyl ether cyclodextrin with one or more of amine, metal ion and ammonium ion.

According to some embodiments of the liposome in the present invention, wherein the salt of sulfobutyl ether cyclodextrin is formed by sulfobutyl ether cyclodextrin with one or more of ammonia ($NH_3$), triethylamine (TA), triethanolamine (TEA), sodium ion, potassium ion and calcium ion.

According to some embodiments of the liposome in the present invention, wherein the active compound is an weak alkalescent compound, preferably one or more selected from vinorelbine, vincristine, topotecan and irinotecan.

According to some embodiments of the liposome in the present invention, wherein the bilayer comprises phospholipid, cholesterol and hydrophilic polymer-modified lipid.

In the present invention, any suitable metal cation ionophores known in the field can be used, such as nikkomycin, A23187 and ionomycin.

In another aspect, the present invention provides a process for preparing the liposome of the present invention described above, comprising:

(1) hydrating lipid phase powders with aqueous solution of sulfobutyl ether cyclodextrin or its salt, to form a blank liposome comprising the aqueous solution of sulfobutyl ether cyclodextrin or its salt as inner water phase, (2) removing the salt of sulfobutyl ether cyclodextrin in the outer phase of the blank liposome obtained in step (1), to form an anion gradient, (3) adding a metal cation ionophore to the outer phase of the blank liposome, to form a pH gradient, and (4) incubating the blank liposome obtained in step (3) with the active compound in aqueous solution, to encapsulate the active compound into the liposome.

According to a preferred aspect of the preparation method of the present invention, the metal casion ionophore is ionophore A23187.

In a further aspect, the present invention provides a liposomal pharmaceutical preparation, comprising the liposome according to any of the present invention described above and a pharmaceutically acceptable carrier and/or excipient.

According to some embodiments of the liposomal pharmaceutical preparation in the present invention, wherein the carrier and/or excipient comprises osmotic regulator and/or antioxidant.

In another further aspect, the present invention provides use of the liposome according to any of the present invention described above in manufacture of a medicament for treatment of a tumor in a patient, wherein the active compound in the liposome is one or more of vinorelbine, vincristine, topotecan and irinotecan.

DETAILED DESCRIPTION OF THE INVENTION

Figure 1:
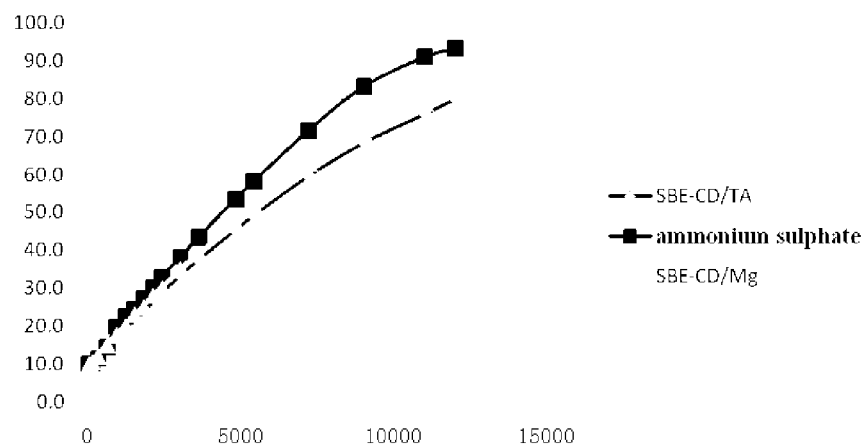
FIG. 1 indicates the in vitro release results of doxorubicin liposomes comparing different inner phases.

The present invention is illustrated by the following examples, which is only exemplary and should not be construed as a limitation to the scope of the present invention.

As used herein, the drug/lipid ratio refers to weight ratio of drug to phospholipid, and "the content of DSPE-mPEG" Refers to its molar percentage in the total phospholipid components in liposomal bilayer.

Example 1

General Process of Preparation of Liposomes with Sulfobutyl Ether Cyclodextrin (SBE-CD) as Inner Water Phase (with the Formulation of SBE-CD)

HSPC, cholesterol and DSPE-mPEG2000 at a mass ratio of 3:1:1 were mixed and dissolved in 95% t-butyl alcohol. The organic solvent was removed by lyophilization to obtain a loose lipid powder. The powder was hydrated with aqueous solution of sulfobutyl ether β-cyclodextrin at 50-60° C. and incubated for 1 hour to obtain a heterogenous multivesicular liposome. The particle size of the liposome was reduced by a micro-jet apparatus. Anion in outer phase of the blank liposome was removed by an ultrafiltration apparatus to form a dynamic transmembrane gradient. An aqueous drug solution was added to the blank liposome at an appropriate drug/lipid ratio, and the drug loading was achieved by incubation at 60° C. for 1 hour.

Example 2

General Process of Preparation of Liposomes with Triethylamine Salt of Sulfobutyl Ether Cyclodextrin as Inner Water Phase (with the Formulation of SBE-CD/TA)

HSPC, cholesterol and DSPE-mPEG2000 at a mass ratio of 3:1:1 were mixed and dissolved in 95% t-butyl alcohol. The organic solvent was removed by lyophilization to obtain a loose lipid powder. The powder was hydrated with aqueous solution of triethylamine salt of sulfobutyl ether cyclodextrin at 50-60° C. and incubated for 1 hour to obtain a heterogenous multivesicular liposome. The particle size of the liposome was reduced by a high pressure extrusion apparatus. Anion in outer phase of the blank liposome was removed by an ultrafiltration apparatus to form a dynamic transmembrane gradient. An aqueous drug solution was added to the blank liposome at an appropriate drug/lipid ratio, and the drug loading was achieved by incubation at 60° C. for 1 hour.

Example 3

General Process of Preparation of Liposomes with Sodium Salt of Sulfobutyl Ether Cyclodextrin as Inner Water Phase (with the Formulation of SBE-CD/Na)

HSPC, cholesterol and DSPE-mPEG2000 at a mass ratio of 3:1:1 were mixed and dissolved in 95% t-butyl alcohol. The organic solvent was removed by lyophilization to obtain a loose lipid powder. The powder was hydrated with aqueous solution of sodium salt of sulfobutyl ether cyclodextrin at 50-60° C. and incubated for 1 hour to obtain a heterogenous multivesicular liposome. The particle size of the liposome was reduced by a high pressure extrusion apparatus. Anion in outer phase of the blank liposome was removed by column chromatography, and then ethanol solution of nikkomycin in an appropriate amount was added (20 ng nikkomycin/1 mg HSPC). The resulting mixture was incubated at 60° C. for ten minutes, so as to exchange hydrogen ion and sodium ion across the liposomal membrane, so as to form a pH gradient. An aqueous drug solution was added to the blank liposome at an appropriate drug/lipid ratio, and the drug loading was achieved by incubation at 60° C. for 1 hour.

Example 4

Comparison of Encapsulation Rate of Liposomes Containing Various Internal Water Phase The liposomes of various drugs with 3 respective inner water phases were prepared as described in Example 1, 2 and 3, at a drug/lipid ratio of 2:9.58 (see table 1).

TABLE 1

Effect of intraliposomal trapping agent on drug loading

| Drug | Encapsulation rate of liposomes having different inner water phases (%) | | |
|---|---|---|---|
| | SBE-CD | SBE-CD/TA | SBE-CD/Na |
| Mitoxatrone hydrochloride | 7.6 | 48.5 | 77.6 |
| Topotecan hydrochloride | 4.8 | 63.6 | 74.6 |
| Irinotecan hydrochloride | 5.3 | 64.1 | 96.1 |
| Doxorubicin hydrochloride | 11.3 | 63.5 | 91.8 |
| Vinorelbine bitartrate | 4.7 | 38.2 | 75.9 |
| Vincristine sulfate | 3.8 | 47.8 | 79.7 |

Conclusion: as can be seen from encapsulation rate as disclosed, the liposome having SBE-CD as inner water phase has a poor encapsulation rate, while high encapsulation rates were achieved with SBE-CD/TA and SBE-CD/Na, which illustrates that a good encapsulation cannot be achieved unless a pH gradient is formed by ion transporting. The drug is firstly protonated after entering inner water phase of the liposome, and then associates with SBE-CD, while drug loading is hardly achieved depending exclusively on inclusion effect of SBE-CD.

Example 5

In Vitro Release of Liposomal Vincristine Formulations Containing Different Inner Water Phase (SBE-CD/TA Vs Ammonium Sulfate)

1, Samples

The vincristine liposomes were prepared at a drug/lipid ratio of 3:9.58, respectively as described in Example 2 for the liposome having SBE-CD/TA as inner water phase, as described in Example 3 for the liposome having SBE-CD/Na as inner water phase, and as described in Example 2, with the exception of the replacement of sulfobutyl ether-β-cyclodextrin triethylamine salt with ammonium sulfate, for the liposome having ammonium sulfate as inner water phase.

2, Release Condition

Samples of liposomal vincristine formulations were diluted by 10 times in release buffer (5 mM $NH_4Cl$/10 mM histidine/260 mM glucose, pH 7.0) and transferred into the dialysis bags. The dialysis was performed against a 200-fold volume of dialysis buffer in dissolution flask. Release test was performed at 37° C., 75 rpm. At various time points (1 h, 2 h, 4 h, 6 h, 8 h, 24 h), aliquots were withdrawn for analysis.

3, Results

TABLE 2

Release of vincristine liposomes with different inner water phases

| Inner water phase | Drug release rate at different time (%) | | | | | | |
|---|---|---|---|---|---|---|---|
| | 1 h | 2 h | 4 h | 6 h | 8 h | 24 h | $t_{1/2}(h)$ |
| SBE-CD/TA | 22 | 31 | 44 | 52 | 61 | 94 | 7.2 |
| SBE-CD/Na | 23 | 31 | 47 | 58 | 68 | 96 | 6.8 |
| ammonium sulfate | 26 | 62 | 91 | 97 | 98 | 99 | 1.1 |

Conclusion: In comparison to the liposome having ammonium sulfate as inner water phase, the liposome having SBE-CD/TA as inner water phase and the liposome having SBE-CD/Na as inner water phase both significantly extended the retention of drug in inner water phase.

Example 6

In Vitro Release of Liposomal Vinorelbine Formulations Containing SBE-CD/$NH_3$ and Ammonium Sulfate as a Mixed Inner Water Phase 1, Samples The vinorelbine liposomes were prepared at a drug/lipid ratio of 3:9.58, as described in Example 2 with the exception of the replacement of sulfobutyl ether-β-cyclodextrin triethylamine salt with the mixed solution of SBE-CD/$NH_3$ and ammonium sulfate as described in A-F of table 3.

TABLE 3

Formulations for Liposomal Vinorelbine having SBE-CD/$NH_3$ and ammonium sulfate as a mixed inner water phase

| Number | Concentration (mM) | |
|---|---|---|
| | [$H^+$] of SBE-CD | Ammonium sulfate |
| A | 280.8 | 86.4 |
| B | 236.7 | 108.9 |
| C | 204.3 | 126.0 |
| D | 180.0 | 138.6 |
| E | 160.2 | 148.5 |
| F | 0 | 225.0 |

2, Release Condition

Samples of liposomal formulations were diluted by 10 times in release buffer (2 mM $NH_4Cl$/10 mM histidine/250 mM glucose, pH 7.5) and transferred into the dialysis bags. The dialysis was performed against a 200-fold volume of dialysis buffer in dissolution flask. Release test was performed at 37° C., 75 rpm. At various time points (1 h, 2 h, 4 h, 8 h), aliquots were withdrawn for analysis.

3, Results

TABLE 4

In vitro release of liposomal vinorelbine formulations having different internal water phase

| Sampling time (h) | Release rate for different inner water phase (%) | | | | | |
|---|---|---|---|---|---|---|
| | A | B | C | D | E | F |
| 1 | 34.9 | 25.1 | 33.2 | 36.0 | 39.1 | 68.3 |
| 2 | 56.6 | 51.8 | 59.0 | 63.1 | 67.7 | 91.5 |
| 4 | 83.6 | 83.5 | 89.3 | 90.2 | 93.4 | 98.6 |
| 8 | 97.4 | 97.2 | 98.0 | 98.5 | 98.6 | 99.3 |

Conclusion: The liposomes having high SBE-CD/NH$_3$ proportion in the mixed inner water phase displayed relatively slow drug release, indicating that ammonium salt of SBE-CD could extend drug release.

Example 7

In Vitro Release of Liposomal Doxorubicin Formulations Containing SBE-CD/TA, SBE-CD/Mg and Ammonium Sulfate Respectively as Inner Water Phase 1, Samples The doxorubicin liposomes were prepared at a drug/lipid ratio of 2:9.58, respectively as described in Example 2 for the liposome having SBE-CD/TA as inner water phase, as described in Example 3 (with the exception of replacing SBE-CD/Na with SBE-CD/Mg and replacing nikkomycin with ionomycin) for the liposome having having SBE-CD/Mg as inner water phase, and as described in Example 2 (with the exception of the replacement of sulfobutyl ether-β-cyclodextrin triethylamine salt with ammonium sulfate) for the liposome having (NH$_4$)$_2$SO$_4$ as inner water phase.

2, Release Condition

Samples were diluted by 200 times in release buffer (50 mM NH$_4$Cl/20 mM histidine/200 mM glucose, pH 6.5) and placed in a water bath of 52° C.±1° C. for incubation. The excitation wavelength for fluorescence spectrophotometer was set at 480 nm, and the emission wavelength at 560 nm. The change of fluorescence was scanned, and the release rate was calculated.

3, Results

TABLE 5

Result of encapsulation rate and particle size of doxorubicin liposomal comprising different inner phases

| Inner water phase | encapsulation rate (%) | particle size (nm) |
|---|---|---|
| (NH$_4$)$_2$SO$_4$ | 100 | 94 |
| SBE-CD/TA | 99.5 | 91 |
| SBE-CD/Mg | 99.8 | 93 |

Note: in this table, the concentration of ammonium ion in the inner water phase of SBE-CD/TA and the concentration of Mg ion in the inner water phase of SBE-CD/Mg were both 500 mM; the concentration of ammonium ion in the inner water phase of SBE-CD/TA in Example 4 is 300 mM; and the concentration of sodium ion in the inner water phase of SBE-CD/Na in Example 4 is 300 mM, so the entrapment rates are different. The same concentration in internal water phase in the formula, similar particle size, and entrapment rate can ensure the in vitro release data more comparable.

Conclusion: In comparison to the liposome having ammonium sulfate as inner water phase, the liposome having SBE-CD/TA as inner water phase and the liposome having SBE-CD/Mg as inner water phase both significantly extended the retention of drug in inner water phase.

Example 8

In Vitro Release of Liposomal Mitoxantrone Formulations Containing SBE-CD/NH$_3$, SBE-CD/Ca and Ammonium Sulfate Respectively as Inner Water Phase 1, Samples The mitoxantrone liposomes were prepared at a drug/lipid ratio of 1:9.58, respectively as described in Example 2 (with the exception of the replacement of sulfobutyl ether-β-cyclodextrin triethylamine salt with ether-β-cyclodextrin arginine salt) for the liposome having SBE-CD/NH$_3$ as inner water phase, as described in Example 3 (with the exception of replacing SBE-CD/Na with SBE-CD/Ca and replacing nikkomycin with calcimycin) for the liposome having having SBE-CD/Ca as inner water phase, and as described in Example 2 (with the exception of the replacement of sulfobutyl ether-β-cyclodextrin triethylamine salt with ammonium sulfate) for the liposome having (NH$_4$)$_2$SO$_4$ as inner water phase.

2, Release Condition

Samples were diluted by 2 times in release buffer (2 M NH$_4$Cl/200 mM histidine, pH 6.5) and placed in a water bath of 52° C.±1° C. for incubation. The samples were taken respectively at time of 0, 5, 15, 30, 60, 120 and 180 min, the encapsulation rates were determined, thereby the release rates can be calculated.

3, Results

TABLE 6

Result of encapsulation rate and particle size of mitoxantrone liposomal comprising different inner phases

| Inner water phase | encapsulation rate (%) | particle size (nm) |
|---|---|---|
| (NH$_4$)$_2$SO$_4$ | 99.0 | 72 |
| SBE-CD/NH$_3$ | 99.2 | 73 |
| SBE-CD/Ca | 99.4 | 72 |

Figure 2:
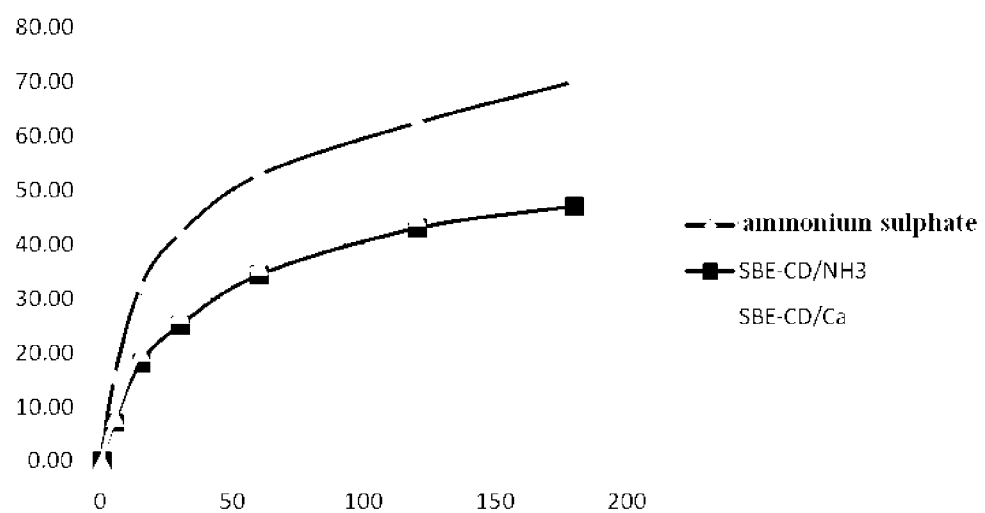
FIG. 2 indicates the in vitro release results of mitoxantrone liposomes comparing different inner phases.

The results of FIG. 2 showed that compared with the liposome containing ammonium sulfate as inner water phase, the liposomes containing SBE-CD/NH$_3$ or SBE-CD/Ca as inner water phase can significantly prolong the retention of the drug in the inner water phase of the liposome.

Example 9

In Vitro Release of Liposomal Topotecan Formulations and Liposomal Irinotecan Formulations Containing SBE-CD/Na, SBE-CD/Ca and Ammonium Sulfate Respectively as Inner Water Phase 1, Samples The topotecan liposomes and irinotecan liposomes were prepared at a drug/lipid ratio of 2:9.58, respectively as described in Example 3 for the liposome having SBE-CD/Na as inner water phase, as described in Example 3 (with the exception of replacing SBE-CD/Na with SBE-CD/Ca and replacing nikkomycin with calcimycin) for the liposome having SBE-CD/Ca as inner water phase, and as described in Example 2 (with the exception of the replacement of sulfobutyl ether-β-cyclodextrin triethylamine salt with ammonium sulfate) for the liposome having (NH$_4$)$_2$SO$_4$ as inner water phase.

2, Release Condition

Samples were diluted by 100 times in release buffer (20 mM NH$_4$Cl/10 mM histidine/250 mM glucose, pH 6.5) and placed in a water bath of 52° C.±1° C. for incubation. For topotecan, the excitation wavelength for fluorescence spectrophotometer was set at 380 nm, and the emission wavelength at 520 nm; for irinotecan, the excitation wavelength for fluorescence spectrophotometer was set at 370 nm, and the emission wavelength at 420 nm. The change of fluorescence was scanned, and the release rate was calculated.

3, Results

TABLE 7

Results of encapsulation rate of topotecan liposome and irinotecan liposome comprising different inner phases

| Inner water phase | encapsulation rate (%) | |
|---|---|---|
| | topotecan | irinotecan |
| $(NH_4)_2SO_4$ | 97.8 | 98.5 |
| SBE-CD/Na | 98.2 | 98.7 |
| SBE-CD/Ca | 98.3 | 99.1 |

Figure 3:
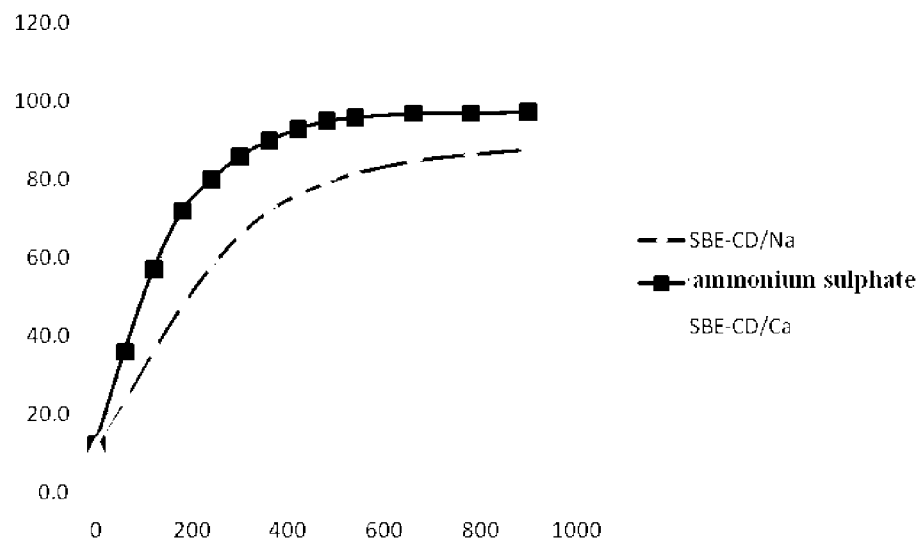
FIG. 3 indicates the in vitro release results of topotecan liposomes comparing different inner phases.
Figure 4:
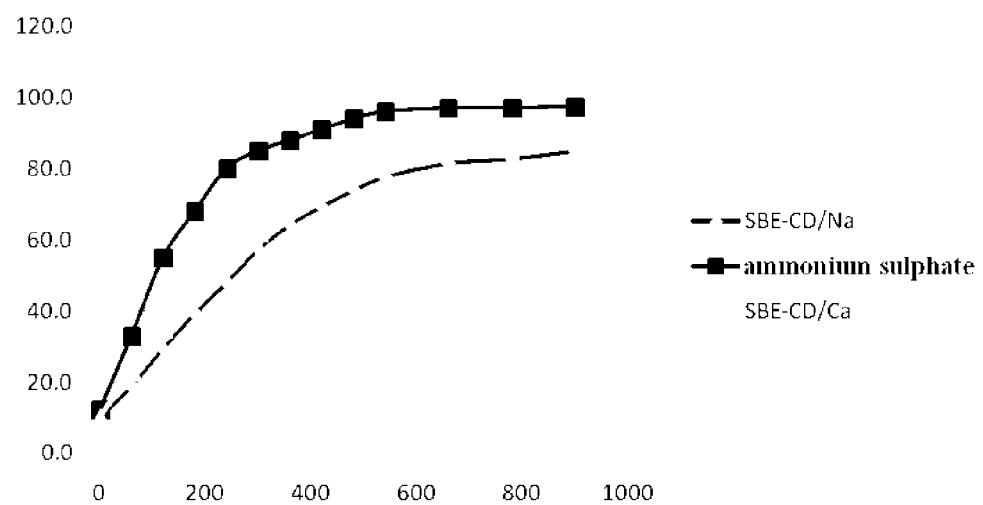
FIG. 4 indicates the in vitro release results of irinotecan liposomes comparing different inner phases.

The results of FIG. 3 and FIG. 4 showed that compared with the liposome containing ammonium sulfate as inner water phase, the SBE-CD/Na and SBE-CD/Ca inner water phases can both significantly prolong the retention of the drugs in the inner water phase of the liposomes.

Example 10

Pharmacokinetics for the Liposomes Having Ammonium Sulfate, Different Ammonium Salts of SBE-CD as Inner Water Phase 1, Samples Vinorelbine, vincristine and irinotecan liposomes were prepared at a drug/lipid ratio of 2:9.58, as described in Example 2 with exception of the replacement of SBE-β-CD/TA with $(NH_4)_2SO_4$ for $(NH_4)_2SO_4$ as inner water phase, as described in Example 2 for SBE-CD/TA as inner water phase, and as described in Example 2 with exception of the replacement of SBE-β-CD/TA with SBE-β-CD/NH$_3$ for SBE-CD/NH$_3$ as inner water phase.

2, Animals and Dosage

This example was conducted in male DBA/2 mice, and the dosage was 10 mg/kg.

3, Results

TABLE 5

Plasma pharmacokinetics of liposome formulations having different inner water phase

| Inner water phase | Half-life for different drug liposome (h) | | |
|---|---|---|---|
| | Vinorelbine | Vincristine | Irinotecan |
| SBE-CD/TA | 4.4 | 67.3 | 8.6 |
| SBE-CD/NH$_3$ | 5.4 | 46.2 | 11.3 |
| $(NH_4)_2SO_4$ | 3.1 | 27.6 | 4.1 |

Conclusion: As shown in pharmacokinetic results, in comparison to the liposome having ammonium sulfate as inner water phase, the liposomes having SBE-CD/NH$_3$ as inner water phase exhibit significantly extended half life.

Example 11

Efficacies of Vinorelbine Liposomes Having Different Inner Water Phase on LLC Tumor Model 1, Formulations Formulation 1: SBE-CD/TA as inner water phase, prepared as described in Example 2.

Formulation 2: Ammonium sulfate as inner water phase, prepared as described in Example 2 with exception of the replacement of SBE-β-CD/TA with ammonium sulfate.

In both formulations, drug/lipid ratio is 3:9.58, and the content of DSPE-mPEG2000 is 0.5%.

2, Experiments

LLC lung cancer cells were collected, and diluted with DMEM medium. After dilution, the tumor cell number was modulated to $2.0 \times 10^6$ cells/ml. 0.2 mL of the tumor cell suspension containing about $4 \times 10^5$ tumor cells was inoculated into forward limb oxter subcutaneous tissue of female C57 mice under aseptic condition. Fourteen days after inoculation, mice were randomized by tumor volume into three groups and administered with a single i.v. injection at a dose of 10 mg/kg.

The mice were bred normally after administration. Tumor diameters were measured to dynamically evaluate anti-tumor efficacies of different formulations. Tumor volume (TV) was calculated with the following formula:

$$TV = \frac{1}{2} \times a \times b^2,$$

in which a and b represent length and width, respectively.

The tumor volumes were calculated by using the measurement results. The experiment data were analyzed using SPSS 11.5 statistics software.

3, Results

TABLE 6 anti-tumor efficacies of vinorelbine liposomes having different inner water phase on LLC tumor model (n = 10, $\bar{x} \pm sd$)

| Day after administration | Tumor volume (mm³) | | |
|---|---|---|---|
| | SBE-CD/TA | ammonium sulfate | 5% glucose solution |
| 0 | 785.0 ± 343.0 | 692.2 ± 259.3 | 780.8 ± 353.3 |
| 1 | 1214.5 ± 732.4 | 979.7 ± 507.3 | 1154.8 ± 618.0 |
| 2 | 1179.6 ± 730.0 | 940.7 ± 415.1 | 1378.2 ± 753.2 |
| 3 | 1420.5 ± 716.3 | 1116.8 ± 503.5 | 1964.3 ± 1004.2 |
| 4 | 1591.6 ± 1056.1 | 1091.6 ± 562.3** | 2456.5 ± 1170.1 |
| 6 | 1665.2 ± 1121.3* | 1353.7 ± 631.6** | 3173.9 ± 1591.2 |
| 7 | 2034.7 ± 1233.8* | 1846.7 ± 1051.5** | 4117.7 ± 2022.8 |
| 9 | 1939.0 ± 1171.0** | 2086.5 ± 1446.8** | 4715.0 ± 2203.6 |
| 11 | 2605.2 ± 1683.3** | 3142.4 ± 1643.0* | 6307.6 ± 3194.9 |

TABLE 6-continued anti-tumor efficacies of vinorelbine liposomes having different inner water phase on LLC tumor model (n = 10, $\bar{x} \pm sd$)

| Day after administration | Tumor volume (mm³) | | |
|---|---|---|---|
| | SBE-CD/TA | ammonium sulfate | 5% glucose solution |
| 12 | 2893.5 ± 1656.5** | 3650.4 ± 1931.8** | 7562.9 ± 3819.7 |
| 14 | 3793.5 ± 2671.7** | 5106.1 ± 2465.1** | 9464.8 ± 4151.7 |

**$P < 0.01$,
*$P < 0.05$, in comparison with 5% glucose control

In comparison with 5% glucose, the growth of tumor was significantly suppressed from day 4 for the liposomes having ammonium sulfate as inner water phase and from day 6 for the liposomes having SBE-CD as inner water phase.

Relative tumor proliferation rate T/C (%) was calculated with the following formula: T/C %=TRTV/CRTV×100%, in which TRTV and CRTV represent relative tumor volume (RTV) of treatment group and of negative control group, respectively. RTV=Vt/Vo. Vo means tumor volume of day 0 (initial dosage), and Vt means tumor volume at each measuring day. Regarding relative tumor volume proliferation rate of SBE-CD group and ammonium sulfate group, the lowest T/C % were 51.8% and 31.1% respectively. That is, anti-tumor efficacy of SBE-CD group on LLC lung cancer was superior to that of ammonium sulfate group.

Example 12

Anti-Tumor Efficacies of Topotecan Liposomes Having Different Inner Water Phase on Prostate RM-1 Tumor Model 1, Formulations Formulation 1: SBE-CD/TA as inner water phase, prepared as described in Example 2.

Formulation 2: Sucrose octasulfate as inner water phase, prepared as described in Example 2 with exception of the replacement of SBE-β-CD/TA with sucrose octasulfate.

In both formulations, drug/lipid ratio is 3:9.58, and the content of DSPE-mPEG2000 is 0.5%.

2, Experiments

RM-1 lung cancer cells were collected, and diluted with 1640 medium. After dilution, the tumor cell number was modulated to $2.0 \times 10^6$ cells/ml. 0.2 mL of the tumor cell suspension containing about $4 \times 10^5$ tumor cells was inoculated into forward limb oxter subcutaneous tissue of female C57 mice under aseptic condition. Twelve days after inoculation, mice were randomized by tumor volume into groups and administered with a single i.v. injection at a dose of 10 mg/kg.

The mice were bred normally after administration. Tumor diameters were measured to dynamically evaluate anti-tumor efficacies of different formulations. Tumor volume (TV) was calculated with the following formula:

$$TV = \tfrac{1}{2} \times a \times b^2,$$

in which a and b represent length and width, respectively.

The tumor volumes were calculated by using the measurement results. The experiment data were analyzed using SPSS 11.5 statistics software.

3, Results

TABLE 7

The antineoplastic effects of topotecan liposomes on RM-1 tumour model (n = 10, $\bar{x} \pm sd$)

| Day after administration | Tumor volume (mm³) | | | |
|---|---|---|---|---|
| | SBE-CD/TA | Sucrose octasulfate | Free topotecan | 5% glucose control |
| 0 | 220.1 ± 70.1 | 218.8 ± 67.3 | 223.0 ± 65.7 | 219.6 ± 60.2 |
| 2 | 339.2 ± 145.0* | 336.8 ± 96.3* | 484.0 ± 154.7 | 468.9 ± 137.7 |
| 4 | 397.3 ± 234.4* | 347.0 ± 117.8** | 606.0 ± 183.1 | 765.3 ± 415.2 |
| 6 | 483.1 ± 253.6** | 500.3 ± 165.5** | 1060.7 ± 393.0 | 1376.9 ± 689.3 |
| 8 | 690.2 ± 656.7* | 640.7 ± 280.7** | 1301.8 ± 563.7 | 2082.9 ± 1508.7 |
| 9 | 914.0 ± 691.4* | 734.2 ± 343.6* | 1628.5 ± 835.4 | 2598.7 ± 2148.2 |
| 13 | 1876.2 ± 1931.9* | 1247.8 ± 858.7** | 3592.9 ± 1523.5 | 4499.4 ± 2946.5 |
| 15 | 2833.9 ± 3016.7* | 2571.1 ± 2844.9** | 6639.3 ± 2388.2 | 7504.9 ± 4335.9 |

**$P < 0.01$,
*$P < 0.05$, in comparison with 5% glucose control group

In comparison with 5% glucose for injection as control, free topotecan did not significantly suppress the growth of tumor (p>0.05), while the tumor growth was significantly suppressed in the two groups of the liposomes having different inner water phase. Significant differences were observed in comparison with free topotecan groups with equal dosages, while no significant difference of the suppression on RM-1 tumor was observed between the two liposomal formulations.

Example 13

Toxicity of Different Liposomal Topotecan Formulations in KM Mice

1, Formulations

Formulation 1: SBE-CD/TA as inner water phase, prepared as described in Example 2.

Formulation 2: Sucrose octasulfate as inner water phase, prepared as described in Example 2 with exception of the replacement of SBE-β-CD/TA with sucrose octasulfate.

In both formulations, drug/lipid ratio is 3:9.58, and the content of DSPE-mPEG2000 is 0.5%.

2, Experiments

Regarding the three liposomal drugs and free drug, each dosage group has two female KM mice, beginning with a maximum dose of 40.6 mg/kg of topotecan and continuing with a descending dose factor of 1.25 (i.e. dosages: 40.6, 32.5, 26.0, 20.8, 16.6, 13.3 and 10.6 mg/kg). Mice was observed in terms of general health and weighed every day for a period of 14 days.

TABLE 8 toxicity of liposomal topotecan formulations having different inner water phase

| Dosage level (mg/kg) | number of dead animals | | | Number of Animals with >15% weight loss | | |
|---|---|---|---|---|---|---|
| | SBE-CD/TA | Sucrose octa-sulfate | Free topotecan | SBE-CD/TA | Sucrose octa-sulfate | Free topotecan |
| 40.6 | 1 | 2 | 1 | 2 | 2 | 2 |
| 32.5 | 1 | 2 | — | 2 | 2 | 1 |
| 26.0 | — | 2 | — | 2 | 2 | — |
| 20.8 | — | 2 | — | 2 | 2 | — |
| 16.6 | — | 2 | — | 2 | 2 | — |
| 13.3 | — | 1 | — | 2 | 1 | — |
| 10.6 | — | 1 | — | 2 | 1 | — |

As shown in Table 8, the order of toxicity was: free topotecan<liposome having SBE-CD/TA as inner water phase<liposome having sucrose octasulfate as inner water phase. The sucrose octasulfate liposome caused animal death in a relative low dosage.

The present inventors further prepared the liposomes of vinorelbine, vincristine and irinotecan, and similarly evaluated their toxicities in KM mice. The same results as that of topotecan were obtained. The order of toxicity was: free drug<liposome having SBE-CD/TA as inner water phase<liposome having sucrose octasulfate as inner water phase. The sucrose octasulfate liposome caused animal death in a relative low dosage.

What is claimed:

1. A liposome comprising bilayer, inner water phase and metal cation ionophore in the outer phase, wherein the inner water phase comprises sulfobutyl ether cyclodextrin, one or more active compounds selected from the group consisting of doxorubicin, epirubicin, pirarubicin, idarubicin and mitoxantrone, and one or more of sodium ion, potassium ion and calcium ion, wherein the sulfobutyl ether cyclodextrin forms precipitate with the active compound in the inner water phase.

2. The liposome according to claim 1, wherein the metal cation ionophore is selected from the group consisting of nikkomycin, A23187 and ionomycin.

3. The liposome according to claim 1, wherein the sulfobutyl ether cyclodextrin is sulfobutyl ether-α-cyclodextrin, sulfobutyl ether-β-cyclodextrin or sulfobutyl ether-γ-cyclodextrin.

4. The liposome according to claim 1, wherein the sulfobutyl ether cyclodextrin has about 6.5 sulfo groups at average per molecule.

5. The liposome according to claim 1, wherein the bilayer comprises phospholipid, cholesterol and hydrophilic polymer-modified lipid.

6. A liposome comprising bilayer and inner water phase, wherein the inner water phase comprises sulfobutyl ether cyclodextrin, one or more active compounds selected from the group consisting of doxorubicin, epirubicin, pirarubicin, idarubicin and mitoxantrone, and one or more of ammonium hydroxide, triethylamine and triethanolamine, wherein the sulfobutyl ether cyclodextrin forms precipitate with the active compound in the inner water phase.

7. The liposome according to claim 6, wherein the sulfobutyl ether cyclodextrin is sulfobutyl ether-α-cyclodextrin, sulfobutyl ether-β-cyclodextrin or sulfobutyl ether-γ-cyclodextrin.

8. The liposome according to claim 6, wherein the sulfobutyl ether cyclodextrin has about 6.5 sulfo groups at average per molecule.

9. The liposome according to claim 6, wherein the bilayer comprises phospholipid, cholesterol and hydrophilic polymer-modified lipid.

10. A process for preparing the liposome according to claim 1, comprising:
    (1) hydrating lipid phase powders with a first aqueous solution of a sulfobutyl ether cyclodextrin salt that comprises one or more of sodium ion, potassium ion and calcium ion, to form a blank liposome comprising the first aqueous solution of the sulfobutyl ether cyclodextrin salt as inner water phase,
    (2) removing the salt of sulfobutyl ether cyclodextrin in the outer phase of the blank liposome, to form an anion gradient,
    (3) adding a metal cation ionophore to the outer phase of the blank liposome, to form a pH gradient, and
    (4) incubating the blank liposome with the active compound in a second aqueous solution, to encapsulate the active compound into the liposome.

11. A liposomal pharmaceutical preparation, comprising the liposome according to claim 1 and a pharmaceutically acceptable carrier and/or excipient.

12. A liposomal pharmaceutical preparation according to claim 11, wherein the carrier and/or excipient comprises osmotic regulator and/or antioxidant.

13. A method of treating a tumor patient, comprising administering a liposome according to claim 1 to the patient in need thereof.

* * * * *